United States Patent [19]

Nickel et al.

[11] Patent Number: 5,215,968
[45] Date of Patent: Jun. 1, 1993

[54] DIPEPTIDE DERIVATIVES HAVING AN ENZYME INHIBITORY ACTION

[75] Inventors: Wolf-Ulrich Nickel, Bad Soden am Taunus; Hansjörg Urbach; Dieter Ruppert, both of Kronberg/Taunus; Bernward Schölkens, Kelkheim, all of Fed. Rep. of Germany

[73] Assignee: Hoechst Aktiengesellschaft, Frankfurt am Main, Fed. Rep. of Germany

[21] Appl. No.: 825,829

[22] Filed: Jan. 28, 1992

Related U.S. Application Data

[63] Continuation of Ser. No. 488,208, Dec. 8, 1989, abandoned.

Foreign Application Priority Data

Dec. 10, 1988 [DE]  Fed. Rep. of Germany ....... 3841732

[51] Int. Cl.$^5$ ............... C07K 5/06; A61K 37/02; C07D 241/04; C07D 277/42
[52] U.S. Cl. ...................... 514/19; 514/18; 514/318; 530/330; 530/331; 546/194; 260/998.2
[58] Field of Search ............ 514/18, 19, 318; 530/330, 331; 546/194; 260/998.2

[56] References Cited

FOREIGN PATENT DOCUMENTS 0273893 7/1988 European Pat. Off. .

OTHER PUBLICATIONS

Haber et al., *J. Cardiovasc. Pharmacol.*, 1987, 10 (Supp. 7), pp. 554–558.
Burger, *Medicinal Chemistry*, Second Edition, Jun. 27, 1960, Interscience Publishers, Inc. New York, N.Y., pp. 565–571, 578–581, 600–601.
Bolis et al., *J. Med. Chem.*, 1987, 30(10), pp. 1729–1737.
Plattner et al., *J. Med. Chem.*, 1988, 31(12), pp. 2277–2288.
Denkewalter et al., *Progress in Drug Research*, 1966, vol. 10, pp. 510–512.

*Primary Examiner*—Ronald W. Griffin
*Attorney, Agent, or Firm*—Finnegan, Henderson, Farabow, Garrett & Dunner

[57] ABSTRACT

Dipeptide derivatives having an enzyme inhibitory action Compounds of the formula I

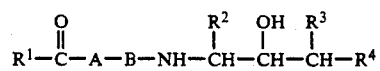

in which $R^1$ represents a (substituted) heterocyclyl-alkyl, -alkoxy, -cycloalkyl or -cycloalkoxy and the corresponding heterocyclylmercapto radicals, A and B independently of one another denote an amino acid, $R^2$ is hydrogen, alkyl, cycloalkyl, cycloalkyl-alkyl, aryl or aryl-alkyl, $R^3$ represents hydrogen, alkyl, aryl, aryl-alkyl or hydroxyl and $R^4$ denotes a radical $(CH_2)_{0-4}CHR^5$-D where $R^5$=hydrogen, alkyl, alkoxy, alkylthio, alkylamino, hydroxyl, azido or halogen and D=(substituted) heterocyclyl, have enzyme-inhibiting properties. Processes for the preparation of compounds of the formula I and their use in the treatment of hypertension and viral diseases are described.

5 Claims, No Drawings

DIPEPTIDE DERIVATIVES HAVING AN ENZYME INHIBITORY ACTION

This application is a continuation of application Ser. No. 07/448,208, filed Dec. 8, 1989, now abandoned.

The invention relates to dipeptide derivatives which inhibit the action of the naturally occurring enzyme renin and viral aspartylproteases, and processes for their preparation and their use.

Dipeptide derivatives and their use as renin inhibitors are known from EP-A-172,346, EP-A-172,347, EP-A-189,203, EP-A-229,667, EP-A-230,266, EP-A-255,082, EP-A-273,893 and EP-A-274,259.

Novel dipeptide derivatives which inhibit the enzyme renin highly effectively in vitro and in vivo have now been found.

The invention relates to compounds of the formula I

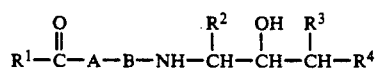

in which $R^1$ denotes Het-$(C_1-C_6)$-alkyl, Het-$(C_1-C_6)$-alkoxy, Het-$(C_3-C_8)$-cycloalkyl, Het-$(C_3-C_8)$-cycloalkyl-$(C_1-C_4)$-alkyl, Het-$(C_3-C_8)$-cycloalkoxy, Het-$(C_3-C_8)$-cycloalkoxy-$(C_1-C_4)$-alkyl, Het-mercapto-$(C_1-C_6)$-alkyl, Het-mercapto-$(C_3-C_8)$-cycloalkyl, Het-mercapto-$(C_3-C_8)$-cycloalkyl-$(C_1-C_4)$-alkyl, Het-mercapto-$(C_1-C_6)$-alkoxy, or Het-mercapto-$(C_3-C_8)$-cycloalkoxy, in which Het represents a 5- to 7-membered monocyclic or 8- to 10-membered bicyclic heterocyclic ring, which can be benzo-fused, aromatic, partly hydrogenated or completely hydrogenated, can contain one, two or three identical or different radicals from the group comprising N, O, S, NO, SO and $SO_2$ as hetero elements and can be substituted by one or two identical or different radicals from the group comprising $(C_1-C_6)$-alkyl, $(C_1-C_6)$-alkoxy, $(C_1-C_6)$-alkoxycarbonyl, hydroxyl, halogen, amino, mono- or di-$(C_1-C_6)$-alkylamino and oxido;

$R^2$ denotes hydrogen, $(C_1-C_{10})$-alkyl, $(C_4-C_7)$-cycloalkyl, $(C_4-C_7)$-cycloalkyl-$(C_1-C_4)$-alkyl, $(C_6-C_{14})$-aryl or $(C_6-C_{14})$-aryl-$(C_1-C_4)$-alkyl;

$R^3$ denotes hydrogen, $(C_1-C_{10})$-alkyl, $(C_6-C_{14})$-aryl, $(C_6-C_{14})$-aryl-$(C_1-C_4)$-alkyl or hydroxyl;

$R^4$ denotes a radical of the formula II $$(CH_2)_m-CHR^5-D \quad (II)$$

wherein $R^5$ represents hydrogen, $(C_1-C_7)$-alkyl, $(C_1-C_5)$-alkoxy, $(C_1-C_5)$-alkylthio, $(C_1-C_5)$-alkylamino, hydroxyl, azido, fluorine, chlorine, bromine or iodine, D denotes a Het radical, wherein Het represents a 5- to 7-membered heterocyclic ring which can be benzo-fused, aromatic, partly hydrogenated or completely hydrogenated, can contain one or two identical or different radicals from the group comprising N, O, S, NO, SO and $SO_2$ as hetero atoms and can be substituted by one or two identical or different radicals from the group comprising $(C_1-C_4)$-alkyl, $(C_1-C_4)$-alkoxy, hydroxyl, halogen, amino, mono- or di-$(C_1-C_4)$-alkylamino and $CF_3$, and m denotes 0, 1, 2, 3 or 4; and A and B independently of one another denote a radical of an amino acid from the series comprising phenylalanine, histidine, tyrosine, tryptophan, methionine, leucine, isoleucine, asparagine, aspartic acid, β-2-thienylalanine, β-3-thienylalanine, β-2-furylalanine, β-3-furylalanine, lysine, ornithine, valine, alanine, 2,4-diaminobutyric acid, arginine, 4-chlorophenylalanine, methionine sulfone, methionine sulfoxide, 2-pyridylalanine, 3-pyridylalanine, cyclohexylalanine, cyclohexylglycine, im-methylhistidine, O-methyltyrosine, O-benzyltyrosine, O-tert.-butyltyrosine, phenylglycine, 1-naphthylalanine, 2-naphthylalanine, 4-nitrophenylalanine, norvaline, β-2-benzo[b]thienylalanine, β-3-benzo[b]thienylalanine, 2-fluorophenylalanine, 3-fluorophenylalanine, 4-fluorophenylalanine, norleucine, cysteine, S-methylcysteine, 1,2,3,4-tetrahydroisoquinoline-3-carboxylic acid, homophenylalanine, DOPA, O-dimethyl-DOPA, 2-amino-4-(2-thienyl)-butyric acid, 2-amino-4-(3-thienyl)-butyric acid, 3-(2-thienyl)serine, (Z)-dehydrophenylalanine,(E)-dehydrophenylalanine, 1,3-dioxolan-2-yl-alanine, N-pyrrolylalanine and 1-, 3-, or 4-pyrazolylalanine, which is linked N-terminally with $R^1$ and A and C-terminally with B and NH—$CHR^2$—CHOH—$CHR^3$—$R^4$, and physiologically tolerated salts thereof.

The chirality centers in the compounds of the formula I can have the R-, S- or R-S-configuration.

Alkyl can be straight-chain or branched. The same applies to radicals derived therefrom, such as, for example, alkoxy, alkylthio, alkylamino, dialkylamino, alkanoyl and aralkyl.

By cycloalkyl there are also to be understood alkyl-substituted radicals, such as, for example, 4-methylcyclohexyl or 2,3-dimethylcyclopentyl. $(C_6-C_{14})$-Aryl is, for example, phenyl, naphthyl, biphenylyl or fluorenyl; phenyl is preferred. The same applies to radicals derived therefrom, such as, for example, aryloxy, aroyl, aralkyl and aralkoxy. By aralkyl there is to be understood a substituted or unsubstituted $(C_6-C_{14})$-aryl radical linked with $(C_1-C_6)$-alkyl, such as, for example, benzyl, α- and β-naphthylmethyl, halobenzyl and alkoxybenzyl, although aralkyl would not be restricted to the radicals mentioned.

A Het radical in the sense of the above definition is, for example, pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl or a benzo-fused or cyclopenta-, cyclohexa- or cyclohepta-fused derivative of these radicals. This heterocyclic radical can be substituted on a nitrogen atom by oxido, $(C_1-C_6)$-alkyl, for example methyl or ethyl, phenyl or phenyl-$(C_1-C_4)$-alkyl, for example benzyl, and/or on one or more carbon atoms by $(C_1-C_4)$-alkyl, for example methyl, phenyl, phenyl-$(C_1-C_4)$-alkyl, for example benzyl, halogen, for example chlorine, hydroxyl, $(C_1-C_4)$-alkoxy, for example methoxy, phenyl-$(C_1-C_4)$-alkoxy, for example benzyloxy, or oxo and can be partly saturated and is, for example, 2- or 3-pyrrolyl, phenyl-pyrrolyl, for example 4- or 5-phenyl-2-pyrrolyl, 2-furyl, 2-thienyl, 4-imidazolyl, methylimidazolyl, for example 1-methyl-2-, -4- or -5-imidazolyl, 1,3-thiazol-2-yl, 2-, 3- or 4-pyridyl, 1-oxido-2-, -3- or -4-pyridino, 2-pyrazinyl, 2-, 4- or 5-pyrimidinyl, 2-, 3- or 5-indolyl, substituted 2-indolyl, for example 1-methyl-, 5-methyl-, 5-methoxy, 5-benzyloxy-, 5-chloro- or 4,5-dimethyl-2-indolyl, 1-benzyl-2- or -3-indolyl, 4,5,6,7-tetrahydro-2-indolyl, cyclohepta[b]-5-pyrrolyl, 2-, 3- or 4-quinolyl, 4-hydroxy-2-quinolyl, 1-, 3- or 4-isoquinolyl, 1-oxo-1,2-dihydro-3-isoquinolyl, 2-quinoxalinyl, 2-benzofuranyl, 2-benzoxazolyl, 2-benzothiazolyl-, benz[e]indol-2-yl or β-carbolin-3-yl.

Examples of partly hydrogenated or completely hydrogenated heterocyclic rings are dihydropyridinyl, pyrrolidinyl, for example 2-, 3- or 4-N-methylpyrrolidinyl, piperidinyl, piperazinyl, morpholino, thiomorpholino and tetrahydrothiophenyl.

Halogen represents fluorine, chlorine, bromine or iodine, in particular fluorine or chlorine.

By salts of compounds of the formula I there are to be understood, in particular, pharmaceutically usable or non-toxic salts.

Such salts are formed, for example, from compounds of the formula I which contain acid groups, for example carboxyl, with alkali or alkaline earth metals, such as Na, K, Mg and Ca, and with physiologically tolerated organic amines, such as, for example, triethylamine and tri-(2-hydroxyethyl)-amine.

Compounds of the formula I which contain basic groups, for example an amino group or a guanidino group, form salts with inorganic acids, such as, for example, hydrochloric acid, sulfuric acid or phosphoric acid, and with organic carboxylic or sulfonic acids, such as, for example, acetic acid, citric acid, benzoic acid, maleic acid, fumaric acid, tartaric acid and p-toluenesulfonic acid.

Preferred compounds of the formula I are those in which $R^1$ is as defined on page 1;
$R^2$ denotes isobutyl, benzyl or cyclohexylmethyl;
$R^3$ denotes hydrogen, $(C_1-C_5)$-alkyl, $(C_6-C_{10})$-aryl, $(C_6-C_{10})$-aryl-$(C_1-C_4)$-alkyl or hydroxyl;
$R^4$ denotes a radical of the formula II, in which
$R^5$ represents hydrogen, $(C_1-C_4)$-alkyl, $(C_1-C_4)$-alkoxy, $(C_1-C_4)$-alkylthio, $(C_1-C_4)$-alkylamino, hydroxyl, azido, fluorine, chlorine, bromine or iodine,
D is defined as the radical Het on page 2 and
m denotes 0, 1 or 2; and
A and B independently of one another denote a divalent radical from the series comprising phenylalanine, histidine, tyrosine, tryptophan, methionine, leucine, isoleucine, asparagine, aspartic acid, β-2-thienylalanine, β-3-thienylalanine, β-2-furylalanine, β-3-furylalanine, lysine, ornithine, valine, alanine, 2,4-diaminobutyric acid, arginine, 4-chlorophenylalanine, methionine sulfone, methionine sulfoxide, 2-pyridylalanine, 3-pyridylalanine, cyclohexylalanine, cyclohexylglycine, im-methylhistidine, O-methyltyrosine, O-benzyltyrosine, O-tert.-butyltyrosine, phenylglycine, 1-naphthylalanine, 2-naphthylalanine, 4-nitrophenylalanine, norvaline, norleucine, cysteine, S-methylcysteine, 1,2,3,4-tetrahydroisoquinoline-3-carboxylic acid, homophenylalanine, 2-amino-4-(2-thienyl)-butyric acid, 2-amino-4-(3-thienyl)-butyric acid, 3-(2-thienyl)-serine, (Z)-dehydrophenylalanine, (E)-dehydrophenylalanine, 1,3-dioxolan-2-yl-alanine, N-pyrrolylalanine and 1-, 3- or 4-pyrazolylalanine,
and physiologically tolerated salts thereof.

Particularly preferred compounds of the formula I are those in which $R^1$ denotes Het-$(C_1-C_4)$-alkyl, Het-$(C_1-C_4)$-alkoxy, Het-$(C_5-C_6)$-cycloalkyl, Het-$(C_5-C_6)$-cycloalkoxy, Het-mercapto-$(C_1-C_3)$-alkyl, Het-mercapto-$(C_5-C_6)$-cycloalkyl, Het-mercapto-$(C_1-C_3)$-alkoxy, and Het-mercapto-$(C_5-C_6)$-cycloalkoxy, in which Het represents a 5- to 6-membered heterocyclic ring, such as, for example, furanyl, thienyl, pyrrolyl, imidazolyl, isoxazolyl, thiazolyl, pyrazolyl, triazolyl, pyridyl, pyrimidyl, pyrazinyl, pyridazinyl, triazinyl, pyrrolidyl, piperidyl, piperazinyl, morpholino, thiomorpholino, tetrahydrofuranyl, tetrahydropyranyl or tetrahydrothienyl, and can be substituted by one or two identical or different radicals from the group comprising $(C_1-C_4)$-alkyl, $(C_1-C_4)$-alkoxy, $(C_1-C_4)$-alkoxycarbonyl, hydroxyl, amino, mono- or di-$(C_1-C_4)$-alkylamino and oxido;

$R^2$ denotes isobutyl, benzyl or cyclohexylmethyl;
$R^3$ denotes hydrogen or hydroxyl;
$R^4$ denotes a radical of the formula II in which
$R^5$ represents hydrogen or fluorine,
D represents a 2-, 3- or 4-pyridine radical, a 2-, 4- or 5-imidazole radical or a 2-oxazoline radical, it being possible for the heterocyclic radicals mentioned in each case to be substituted by one or two radicals from the group comprising methyl, methoxy, fluorine, chlorine, bromine and $CF_3$, and
m denotes 0, 1 or 2; and
A and B independently of one another denote a divalent radical from the series comprising phenylalanine, histidine, tyrosine, tryptophan, methionine, leucine, isoleucine, asparagine, aspartic acid, β-2-thienylalanine, β-3-thienylalanine, β-2-furylalanine, lysine, ornithine, valine, alanine, 2,4-diaminobutyric acid, arginine, 4-chlorophenylalanine, methionine sulfone, methionine sulfoxide, 2-pyridylalanine, 3-pyridylalanine, cyclohexylalanine, cyclohexylglycine, im-methylhistidine, O-methyltyrosine, O-benzyltyrosine, O-tert.-butyltyrosine, phenylglycine, 1-naphthylalanine, 2-naphthylalanine, 4-nitrophenylalanine, norvaline, norleucine, 1,2,3,4-tetrahydroisoquinoline-3-carboxylic acid, homophenylalanine, 2-amino-4-(2-thienyl)-butyric acid and 1-, 3- and 4-pyrazolylalanine,
and physiologically tolerated salts thereof.

The invention furthermore relates to a process for the preparation of compounds of the formula I, which comprises coupling a fragment having a terminal carboxyl group or a reactive derivative thereof with a corresponding fragment having a free amino group, if appropriate splitting off (a) protective group(s) temporarily introduced for protection of other functional groups and if appropriate converting the compound thus obtained into its physiologically tolerated salt.

Fragments of a compound of the formula I having a terminal carboxyl group have the following formulae IIIa, IIIb and IIIc:

Fragments of a compound of the formula I having a terminal amino group have the following formulae IVa, IVb and IVc:

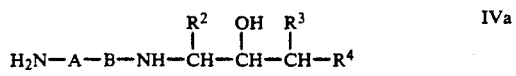

-continued

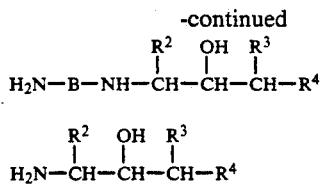

Methods which are suitable for the preparation of an amide bond are described, for example, in Houben-Weyl, Methoden der organischen Chemie (Methods of Organic Chemistry), Volume 15/2; Bodanszky et al., Peptide synthesis, 2nd ed. (Wiley & Sons, New York 1976) or Gross, Meienhofer, The Peptides. Analysis, synthesis, biology (Academic Press, New York 1979). The following methods are preferably used: active ester method using N-hydroxy-succinimide or 1-hydroxybenzotriazole as the ester component, coupling with a carbodiimide, such as dicyclohexylcarbodiimide, or with propanephosphonic anhydride and the mixed anhydride method using pivaloyl chloride.

The preparation of the optically active amines, used as starting compounds, of the formula IVc

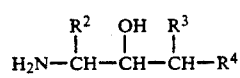

in which $R^2$, $R^3$ and $R^4$ are as defined above, is carried out starting from optically active α-amino acids, the center of asymmetry thereof being retained. For this, an N-protected amino acid aldehyde is prepared in a known manner and is coupled to a corresponding heteroarylalkyl unit in an aldol-analogous addition to give, after splitting off of the N-protective group, aminoalcohols of the formula IVc. Diastereomer mixtures in respect of the center carrying OH are obtained and are resolved in a manner which is known per se, for example by fractional crystallization or by chromatography. The diastereomer purity is checked by means of high performance liquid chromatography, and the enantiomer purity can be checked in a known manner by conversion into Mosher derivatives (H. S. Mosher et al., J. org. Chem. 34, 2543 (1969)).

The preparation of N-protected amino acid aldehydes is carried out in accordance with the method of B. Castro et al. (Synthesis 1983, 676).

The aldol-analogous addition onto N-protected amino acid aldehydes (preferably N-tert.-butoxycarbonyl and -benzyloxycarbonyl protective groups) is carried out in a solvent which is inert towards bases, such as ether, tetrahydrofuran, toluene, dimethylformamide, dimethyl sulfoxide or dimethoxyethane.

Bases which can be used for deprotonation of the heteroarylalkyl component are alkali metal alcoholates, such as potassium tert.-butylate or sodium methylate, alkali metal hydrides, such as sodium hydride or potassium hydride, organometallic bases, such as n-butyllithium, s-butyllithium, methyllithium or phenyllithium, sodium amide and alkali metal salts of organic nitrogen bases, such as lithium diisopropylamide.

The preliminary and subsequent operations required for the preparation of compounds of the formula I, such as introduction and splitting off of protective groups, are known from the literature and are described, for example, in T. W. Greene, "Protective Groups in Organic Synthesis". Salts of compounds of the formula I with salt-forming groups are prepared in a manner which is known per se, for example by reacting a compound of the formula I having a basic group with a stoichiometric amount of a suitable acid. Stereoisomer mixtures, in particular diastereomer mixtures, which are obtained when racemic amino acids A or B are used, can be resolved in a manner which is known per se by fractional crystallization or by chromatography.

The compounds of the formula I according to the invention have enzyme-inhibiting properties; in particular, they inhibit the action of the naturally occurring enzyme renin. Renin is a proteolytic enzyme from the aspartyl protease class, which is secreted by juxtaglomerular cells of the kidneys into the blood circulation as a consequence of various stimuli (volume depletion, sodium deficiency or β-receptor stimulation). In the blood circulation, it splits off the decapeptide angiotensin I from the angiotensinogen secreted by the liver. This is converted into angiotensin II by the "angiotensin converting enzyme" (ACE). Angiotensin II plays an essential role in blood pressure regulation, since it increases the blood pressure directly by vasocontraction. It additionally stimulates the secretion of aldosterone from the adrenals and in this way, via inhibition of sodium excretion, increases the extracellular fluid volume, which in turn contributes towards an increase in blood pressure. Inhibitors of the enzymatic activity of renin have the effect of reduced formation of angiotensin I, which results in a reduced formation of angiotensin II. The reduction in the concentration of this active peptide hormone is the direct cause of the antihypertensive action of renin inhibitors.

The activity of renin inhibitors can be investigated by in vitro tests. In these, the reduction of the formation of angiotensin I is measured in various systems (human plasma or purified human renin).

1. Test principle

For example, human plasma containing both renin and angiotensinogen is incubated at 37° C. with the compound to be tested. During this incubation, angiotensin I is liberated from angiotensinogen under the action of renin, and can then be measured with a commercially available radioimmunoassay method. This liberation of angiotensin is inhibited by renin inhibitors.

2. Obtaining the plasma

Blood is obtained from volunteer subjects (about 0.5 l per person; Bluko withdrawal apparatus from ASID Bonz und Sohn, Unterschleißheim) and is collected in partly evacuated bottles, while cooling with ice. Coagulation is prevented by addition of EDTA (final concentration 10 mM). After centrifugation (Rotor HS 4 (Sorvall), 3,500 revolutions per minute, 0°-4° C., 15 minutes; repetition if necessary), the plasma is carefully pipetted off and frozen in suitable portions at −30° C. Only plasmas of sufficiently high renin activity are used for the test. Plasmas of low renin activity are activated by a low temperature treatment (−4° C., 3 days); (prorenin→renin).

3. Test procedure

Angiotensin I is determined using a Renin-Maia ® kit (Serono Diagnostics S.A., Coinsins, Switzerland). The incubation of the plasma is carried out in accordance with the instructions given with the kit:

Incubation batch: 1,000 μl of plasma (thawed at 0°-4° C.)

100 µl of phosphate buffer (pH 7.4 addition of $10^{-4}$M Ramiprilat)
10 µl of PMSF solution
10 µl of 0.1% Genapol PFIC
12 µl of DMSO and test preparation The test preparations are in general dissolved in an amount of $10^{-2}$M in 100% dimethyl sulfoxide (DMSO) and the solutions are diluted accordingly with DMSO; the incubation batch contains not more than 1% of DMSO.

The batches are mixed in ice and placed in a waterbath (37° C.) for 1 hour for incubation. A total of 6 samples (in each case 100 µl) are taken from an additional batch without inhibitor and without further incubation for determination of the starting angiotensin I content of the plasma used.

The concentrations of the test preparations are chosen so that approximately the range from 10 to 90% enzyme inhibition is covered (at least five concentrations). At the end of the incubation time, three 100 µl samples from each batch are frozen in pre-cooled Eppendorf vessels on dry ice and stored at about −25° C. for the angiotensin I determination (mean value of three individual samples).

Angiotensin I radioimmunassay (RIA)

The use instructions of the RIA kit (Renin-Maia ® kit, Serono Diagnostics S.A., Coinsins, Switzerland) are followed exactly.

The calibration curve comprises the range from 0.2 to 25.0 ng angiotensin I per ml. The basal angiotensin I content of the plasma is subtracted from all the measurement values. The plasma renin activity (PRA) is stated as ng of angiotensin I/ml×hour. PRA values in the presence of the test substances are based on a batch without inhibitor (=100%) and are stated as % residual activity. The $IC_{50}$ value is read off from the plot of % residual activity against the concentration (M) of the test preparation (logarithmic scale).

The compounds of the general formula I described in the present invention exhibit inhibiting actions in the in vitro test at concentrations of about $10^{-5}$ to $10^{-10}$ mol/l.

Renin inhibitors cause a reduction in blood pressure in salt-depleted animals. Since human renin differs from the renin of other species, primates (marmosets, Rhesus monkeys) are used for the in vivo test on renin inhibitors. Primate renin and human renin are largely homologous in their sequence. Endogenous renin secretion is stimulated by intravenous injection of furosemide. The test compounds are then administered and their action on blood pressure and heart rate is measured. The compounds of the present invention are active here in a dose range of about 0.1–5 mg/kg intravenously, and in the dose range of about 1–50 mg/kg on intraduodenal administration by gastroscope. The compounds of the general formula I described in the present invention can be used as antihypertensives and for the treatment of cardiac insufficiency.

HIV protease is cut out autocatalytically from GAG-POL polypeptide and then splits the precursor peptide p55 into the core antigens p17, p24 and p14. It is thus an essential enzyme, inhibition thereof interrupts the life cycle of the virus and suppresses its multiplication.

In biological tests, it has been found that the compounds according to the invention have an enzyme inhibitory action and also inhibit viral enzymes, such as HIV protease. The HIV protease-inhibiting action is of particular importance and qualifies the compounds according to the invention in particular for the therapy and prophylaxis of diseases caused by infection with HIV. The compounds of the general formula I according to the invention exhibit inhibiting actions at concentrations of about $10^{-4}$ to $10^{-8}$ mol/l in the in vitro tests used.

The invention furthermore relates to the use of compounds of the formula I for the preparation of pharmaceuticals for the therapy of hypertension and in the treatment of congestive cardiac insufficiency, as well as for the therapy and prophylaxis of virus diseases, in particular diseases caused by HIV, as well as to the pharmaceuticals mentioned.

Pharmaceutical preparations contain an effective amount of the active compound of the formula I together with an inorganic or organic pharmaceutically usable excipient. They can be used intranasally, intravenously, subcutaneously or perorally. The dosage of the active compound depends on the warm-blooded species, body weight, age and mode of administration.

The pharmaceutical preparations of the present invention are prepared by dissolving, mixing, granulating or coating processes which are known per se.

For an oral use form, the active compounds are mixed with the additives customary for this, such as excipients, stabilizers or inert diluents, and are brought by customary methods into suitable presentation forms, such as tablets, coated tablets, push-fit capsules, aqueous, alcoholic or oily suspensions or aqueous, alcoholic or oily solutions. Inert excipients which can be used are, for example, gum arabic, magnesia, magnesium carbonate, potassium phosphate, lactose, glucose, magnesium stearyl fumarate or starch, in particular maize starch. The formulation can be carried out on either dry or moist granules. Examples of oily excipients or solvents are vegetable or animal oils, such as sunflower oil and cod-liver oil.

For subcutaneous or intravenous administration, the active compounds or physiologically tolerated salts thereof are brought into solutions, suspensions or emulsions, if desired with the substances customary for these, such as solubilizing agents, emulsifiers or other auxiliaries. Examples of possible solvents are: water, physiological saline solutions or alcohols, for example ethanol, propanediol or glycerol, and in addition also sugar solutions, such as glucose solutions or mannitol solutions, or also a mixture of the various solvents mentioned.

| List of abbreviations used: | |
|---|---|
| Boc | tert.-butoxycarbonyl |
| TLC | thin layer chromatography |
| DCC | dicyclohexylcarbodiimide |
| DNP | 2,4-dinitrophenyl |
| DMF | dimethylformamide |
| DMSO | dimethyl sulfoxide |
| Fmoc | 9-fluorenylmethoxycarbonyl |
| EA | ethyl acetate |
| FAB | fast atom bombardment |
| HOBt | 1-hydroxybenzotriazole |
| Iva | isovaleryl |
| M | molecular peak |
| MeOH | methanol |
| MS | mass spectrum |
| R.T. | room temperature |
| m.p. | melting point |
| Thi | β-2-thienylalanine |
| THF | tetrahydrofuran |

| List of abbreviations used: | |
|---|---|
| Z | benzyloxycarbonyl |

The other abbreviations used for amino acids correspond to the three-letter code customary in peptide chemistry, such as is described, for example, in Eur. J. Biochem. 138, 9-37 (1984). Unless expressly stated otherwise, the amino acids always have the L-configuration.

The following examples serve to illustrate the present invention, without this being limited thereto.

EXAMPLE 1

N-(2-Amino-thiazol-4-yl-acetyl)-L-Phe-L-Nva-(1-S-cyclohexylmethyl-2-S-hydroxy-5-(2-pyridyl))-n-pentylamide 100 mg of N-(N-triphenylmethyl-2-amino-thiazol-4-ylacetyl)-L-Phe-L-Nva-(1-S-cyclohexylmethyl-2-S-hydroxy-5-(2-pyridyl))-n-pentylamide were stirred in a mixture of formic acid/water 5:1 at R.T. for 5 hours. The triphenylmethanol which had precipitated out was then filtered off with suction and rinsed with water and the aqueous solution was concentrated in vacuo. The residue was taken up in ethyl acetate, the solution was washed neutral twice with dilute NaHCO$_3$ solution and then washed with saturated NaCl solution and dried over MgSO$_4$, the desiccant was filtered off and the filtrate was concentrated.

The yield was 57 mg.
Melting point: 87° C.
MS (FAB): 664 (M$^+$+1)

EXAMPLE 2

N-(N-Triphenylmethyl-2-amino-thiazol-4-yl-acetyl)-L-Phe-L-Nva-(1-S-cyclohexylmethyl-2-S-hydroxy-5-(2-pyridyl))-n-pentylamide 262 mg of N-(N-triphenylmethyl-2-amino-thiazol-4-ylacetyl)-L-phenylalanine were dissolved in 5 ml of DMF together with 81 mg of HOBt, 109 mg of DCC and 67 μl of NEM and the solution was stirred at R.T. for 1 hour. Thereafter, 180 mg of L-norvalin-(1-S-cyclohexylmethyl-2-S-hydroxy-5-(2-pyridyl))-n-pentylamide, dissolved in 2 ml of DMF, were added. The reaction mixture was stirred at R.T. for 48 hours. It was then diluted with water, the dicyclohexylurea which had precipitated was filtered off and the solution was concentrated in vacuo. The residue was taken up in ethyl acetate and the mixture was washed three times with saturated NaHCO$_3$ solution, washed twice with saturated NaCl and then dried over MgSO$_4$ and concentrated. After purification by chromatography on silica gel (CH$_2$Cl$_2$/MeOH 20:1), 210 mg of product were obtained.

Melting point: 75° C.
MS (FAB): 906 (M$^+$+1)

EXAMPLE 3

N-(N-Triphenylmethyl-2-amino-thiazol-4-yl-acetyl)-L-phenylalanine a) 3.2 g of N-triphenylmethyl-2-amino-thiazol-4-yl acetic acid, 1.34 g of HOBt, 1.81 g of DCC, 1.43 g of L-Phe-OMe and 1 ml of N-ethylmorpholine were dissolved in succession in 30 ml of DMF (absolute) and the solution was stirred overnight. After 24 hours, a little water was added, the dicyclohexylurea which had precipitated was filtered off and the resulting solution was concentrated in vacuo. The residue was taken up in ethyl acetate, the mixture was washed three times with dilute NaHCO$_3$ solution, twice with 10% strength citric acid and twice with saturated NaCl solution and the organic phase was dried over MgSO$_4$ and then concentrated. Column chromatography over silica gel using cyclohexane/EA gave 3.6 g of the methyl ester as an oil.

b) 3.5 g of the methyl ester obtained under a) were stirred with an equimolar amount of 1N sodium hydroxide solution in 30 ml of a dioxane-water mixture (1:1) at R.T. for 3 hours. Thereafter, the reaction solution was freed from the dioxane in vacuo and extracted with diethyl ether, and the aqueous phase was acidified to pH 3 and extracted intensively three times with ethyl acetate. The organic phase was dried over MgSO$_4$, the desiccant was filtered off and the filtrate was concentrated in vacuo. The yield of the colorless solid was 2.7 g.
Melting point: 205°-208° C.

EXAMPLE 4

N-tert.-Butoxycarbonyl-norvalyl-(1-S-cyclohexylmethyl-2-S-hydroxy-5-(2-pyridyl))-n-pentylamide 2.1 g of N-tert.-butoxycarbonylnorvaline, 1.6 g of HOBt, 2.1 g of DCC and 1.4 ml of N-ethylmorpholine were dissolved in 50 ml of DMF (absolute). 2.6 g of 2-S-amino-1-cyclohexyl-3-S-hydroxy-6-(2-pyridyl)-hexane, dissolved in 5 ml of DMF, were added to this mixture at 0° C. The solution was stirred at R.T. for 48 hours. 5 ml of water were then added, the dicyclohexylurea which had precipitated was filtered off and the filtrate was diluted with 150 ml of ethyl acetate. This phase was extracted three times with saturated NaHCO$_3$ solution, twice with saturated NaCl solution and twice with water. The organic phase which remained was dried over MgSO$_4$ and concentrated in vacuo and the residue was chromatographed over silica gel using CH$_2$Cl$_2$/MeOH. 3.56 g were obtained as a viscous oil.
Optical rotation: $\alpha_D^{22} = -47.4°$ C. (c=1.135, methanol)
MS (FAB): 476 (M$^+$+1)

EXAMPLE 5

L-Nva-(1-S-Cyclohexylmethyl-2-S-hydroxy-5-(2-pyridyl)-n-pentylamide 200 mg of the compound described in Example 4 were dissolved in 3 ml of trifluoroacetic acid at 0° C. and the mixture was left to stand for 30 minutes. After warming to R.T., the excess trifluoroacetic acid was stripped off in vacuo, the residue was dissolved in ethyl acetate and the solution was extracted three times with dilute NaHCO$_3$ solution. The organic phase was washed with saturated NaCl solution and water and dried over MgSO$_4$, the desiccant was filtered off and the filtrate was concentrated. An oil was obtained. The amino acid derivative from which the N-terminal protection was removed in this manner was used very quickly for further reactions.
MS (FAB): 376 (M$^+$+1)

EXAMPLE 6

N-(S-(4-Pyridyl)-mercaptoacetyl)-L-phenylalanine

The title compound was prepared from (4-pyridyl)-mercaptoacetic acid and L-phenylalanine methyl ester by the process described in Example 3.
Melting point: 199°-201° C.

$^1$H-NMR (60 MHz, d$_6$-DMSO): δ=3.05 (2H, CH$_2$; 3.8 (2H, CH$_2$CO); 4.5 (m, 1H, C-H$_α$), 7.30 (s, 5H, phenyl); 8.0-8.7 (m, 4H, pyridyl) ppm
MS (DCI): 317 (M$^+$+1).

EXAMPLE 7

N-(S-(4-Pyridyl)-mercaptoacetyl)-L-Phe-L-Nva-(1-S-cyclohexylmethyl-2-S-hydroxy-5-(2-pyridyl))-n-pentylamide The title compound was prepared from the phenylalanine derivative described in Example 6 and from the norvaline derivative described in Example 5 by the process described in Example 2.
MS (FAB): 674 (M$^+$+1)

EXAMPLE 8

N-(2-Pyridyl)-ethoxycarbonyl-L-Phe-L-Nva-OH
The title compound was prepared from N-(2-pyridyl)-ethoxycarbonyl-L-phenylalanine and L-Nva-OMe by the process described in Example 3a) and subsequent ester hydrolysis described in Example 3b).
MS (FAB): 414 (M$^+$+1)

EXAMPLE 9

N-(2-Pyridyl)-ethoxycarbonyl-L-Phe-L-Nva-(1-S-cyclohexylmethyl-2-S-hydroxy-5-(2-pyridyl))-n-pentylamide
The title compound was obtained from the dipeptide described in Example 8 and 2-S-amino-1-S-cyclohexyl-3-S-hydroxy-6-(2-pyridyl)-hexane by the process described in Example 4.
MS (FAB): 672 (M$^+$+1)

EXAMPLE 10

N-(3-Pyridyl)-ethoxycarbonyl-L-Phe-L-Nva-(1-S-cyclohexylmethyl-2-S-hydroxy-5-(2-pyridyl))-n-pentylamide
The title compound was prepared from N-(3-pyridyl)-ethoxycarbonyl-L-Phe and the compound described in Example 5 by the process described in Example 2.
Melting point: 46°-50° C.
MS (FAB): 672 (M$^+$+1).

EXAMPLE 11

N-(4-Pyridyl)-ethoxycarbonyl-L-Phe-L-Nva-(1-S-cyclohexylmethyl-2-S-hydroxy-5-(2-pyridyl))-n-pentylamide
The title compound was obtained from N-(4-pyridyl)-ethoxycarbonyl-L-Phe and the compound described in Example 5 by the process described in Example 2. MS (FAB): 672 (M$^+$+1)

EXAMPLE 12

Fmoc-His(Trt)-(1-S-Cyclohexylmethyl-2S-hydroxy-5-(2-pyridyl))-n-pentylamide
1.2 g of Fmoc-His(Trt)-OH, 340 mg of HOBt, 445 mg of DCC and 0.3 ml of NEM were dissolved in 11 ml of DMF and the solution was stirred at R.T. for 1 hour. 580 mg of 2-S-amino-1-S-cyclohexyl-3-S-hydroxy-6-(2-pyridyl)-hexane, dissolved in 4 ml of DMF, were added to this mixture and the mixture was stirred overnight. After addition of 5 ml of water, the urea which had precipitated out was filtered off and the product was taken up in 100 ml of ethyl acetate. The organic phase was washed three times with saturated NaHCO$_3$ solution and twice with saturated NaCl solution and was then dried over MgSO and, after filtration, concentrated in vacuo. The residue was chromatographed over silica gel (CH$_2$Cl$_2$/MeOH). The yield of the compound mentioned was 1.06 g.
Melting point: 85° C.

EXAMPLE 13

L-His(Trt)-(1-S-Cyclohexylmethyl-2-S-hydroxy-5-(2-pyridyl))-n-pentylamide
500 mg of the compound described in Example 12 were dissolved in 5 ml of DMF (absolute) together with 0.6 ml of diethylamine and the solution was stirred at R.T. for 20 minutes. Thereafter, the solvent was stripped off under a high vacuum and the residue which remained was chromatographed over silica gel using CH$_2$Cl$_2$/MeOH. 320 mg of the title compound were isolated in this manner.
MS (FAB): 656 (M$^+$+1)

EXAMPLE 14

N-(2-Pyridyl)-ethoxycarbonyl-L-Phe-L-His(Trt)-(1-S-cyclohexylmethyl-2-S-hydroxy-5-(2-pyridyl))-n-pentylamide
157 mg of 2-Pyoc-L-Phe, 85 mg of HOBt, 113 mg of DCC and 70 μl of NEM were dissolved in 5 ml of DMF and a solution of 310 mg of the compound from Example 13 in 3 ml of DMF was added. The mixture was stirred for 58 hours and worked up as described in Example 12. 265 mg of the title compound were isolated.
MS (FAB): 953 (M$^+$+1)

EXAMPLE 15

N-(2-Pyridyl)-ethoxycarbonyl-L-Phe-L-His-(1-S-cyclohexylmethyl-2-S-hydroxy-5-(2-pyridyl))-n-pentylamide
115 mg of the compound from Example 14 were stirred in 2.5 ml of trifluoroacetic acid for 1.5 hours. The excess acid was then removed in vacuo, the residue was dissolved in ethyl acetate and the solution was neutralized with dilute NaHCO$_3$ solution. The ethyl acetate solution was dried over MgSO$_4$ and then filtered and concentrated in vacuo. Chromatography of the residue over silica gel using CH$_2$Cl$_2$/MeOH gave 57 mg of the desired product.
Melting point: 68° C.
MS (FAB): 710 (M$^+$+1)

EXAMPLE 16

2-Pyoc-L-methionine
6 g of 2-(2-pyridyl)-ethyl p-nitrophenyl carbonate and 2.5 g of L-Met-OMe were dissolved in 60 ml of acetonitrile, 1N NaOH solution was added until the pH reached 8.5-9.0 and the mixture was stirred until the reaction was complete (TLC control). The acetonitrile was then stripped off in vacuo and the aqueous solution of the reaction mixture was extracted at pH 9, at pH 6 and, after further acidification with 1N HCl, at pH 3 using diethyl ether. The last extraction gave the desired product, which was obtained in purified form in a yield of 2.43 g by column chromatography on silica gel using CH$_2$Cl$_2$/EA. 2.2 g of the oil thus obtained were dissolved in 30 ml of ethanol/water 2:1, and 585 mg of solid NaOH were added. After 2 hours, the ethanol was distilled off in vacuo and the aqueous solution was brought to pH 3 and likewise concentrated in vacuo. The residue which remained was stirred with acetone and the organic solution was separated off from the undissolved constituents. After the solution had been dried and concentrated, 1.89 g of the title compound were obtained.

Optical rotation: $\alpha_D^{20} = -9.4°$ (c=1, ethanol)

EXAMPLE 17

N-(2-Pyridyl)-ethoxycarbonyl-L-Met-L-Nva-(1-S-cyclohexylmethyl-2-S-hydroxy-5-(2-pyridyl))-n-pentylamide 167 mg of 2-Pyoc-Met-OH and 190 mg of the compound from Example 5 were reacted by the process of Example 2. After the working up and chromatography described, 64 mg of the title compound were isolated.

Melting point: 104°–105° C.
MS (FAB): 657 (M+ +1)

EXAMPLE 18

4-Pyridylmethyl 4-nitrophenyl carbonate 20.3 g of p-nitrophenyl chloroformate were dissolved in 150 ml of $CH_2Cl_2$ (absolute) and the solution was cooled to 0° C. under $N_2$. 520 mg of 4-dimethylaminopyridine (DMAP) were added and 10 g of 4-hydroxymethylpyridine in 50 ml of $CH_2Cl_2$ (absolute) were then added dropwise to this solution. The mixture was stirred overnight at R.T. and the crystals which had precipitated were filtered off. The crystals were recrystallized using fresh $CH_2Cl_2$ under the influence of heat and, after cooling, were filtered off again.

Yield: 17.5 g.
Melting point: 150°–154° C.

EXAMPLE 19

N-4-Pyridylmethoxycarbonyl-L-phenylalanine 8 g of 4-pyridylmethyl 4-nitrophenyl carbonate and 4.82 g of L-phenylalanine were dissolved in 350 ml of acetonitrile/water 1:1, and about 45 ml of 2N NaOH were added to pH 10. The mixture was stirred overnight and was freed from the acetonitrile in vacuo. The aqueous solution was brought to pH 6, washed three times with diethyl ether, subsequently brought to pH 1 and concentrated to give a solid residue. This was dissolved in water and the solution was extracted intensively with ethyl acetate and then brought to pH 2 and the precipitate which had separated out was filtered off with suction. After drying, the precipitate weighed 7.3 g.

Melting point: 195°–197° C.

The following compounds were prepared analogously to the compound described in Example 19:

EXAMPLE 20

N-(2-(N-Phthalimidyl)-ethoxycarbonyl)-L-phenylalanine

Melting point: 65°–72° C.

EXAMPLE 21

N-(3-Pyridylethoxycarbonyl)-L-phenylalanine hydrochloride

Melting point: 105° C.

EXAMPLE 22

N-(2-Pyridylethoxycarbonyl)-L-methionine sulfone hydrochloride

Melting point: 48° C.

EXAMPLE 23

N-(4-Pyridylethoxycarbonyl)-L-phenylalanine
Melting point: 196°–204° C. (decomposition)

EXAMPLE 24

N-(N-tert.-Butoxycarbonyl-4-piperidyl)-ethoxycarbonyl-L-phenylalanine

MS (DCI): 421 (M+ +1)

EXAMPLE 25

N-(N-tert.-Butoxycarbonyl-2-piperidyl)-ethoxycarbonyl-L-phenylalanine

Melting point: 52° C.

EXAMPLE 26

N-(2-(4-Morpholino)-ethoxycarbonyl)-L-phenylalanine

MS (DCI): 323 (M+ +1) Melting point: 66° C. (sublimation)

EXAMPLE 27

N-(2-(N-Methylpyrrolidin-2-yl)-ethoxycarbonyl)-L-phenylalanine

MS (DCI): 321 (M+ +1)

EXAMPLE 28

N-(2-(4-tert.-Butoxycarbonylpiperazin-1-yl)-ethoxycarbonyl)-L-phenylalanine

MS (DCI): 421 (M+ +1) Melting point: 85° C.

The following compounds were prepared analogously to the compound described in Example 17:

EXAMPLE 29

N-(2-(N-Phthalimidyl)-ethoxycarbonyl)-L-Phe-L-Nva-(1-S-cyclohexylmethyl-2-S-hydroxy-5-(2-pyridyl))-n-pentylamide The title compound was prepared from the compounds of Examples 20 and 5 by the process described in Example 2.

Melting point: 57°–62° C.
MS (FAB): 740 (M+ +1)

EXAMPLE 30

N-(3-Pyridylethoxycarbonyl)-L-Phe-L-His-(1-S-cyclohexylmethyl-2-S-hydroxy-5-(2-pyridyl))-n-pentylamide

MS (FAB): 709 (M+ +1)

EXAMPLE 31

N-(2-Morpholin-4-yl)-ethoxycarbonyl-L-Phe-L-Nva-(1-S-cyclohexylmethyl-2-S-hydroxy-5-(2-pyridyl))-n-pentylamide

MS (FAB): 680 (M+ +1)

EXAMPLE 32

N-(2-(N-Methylpyrrolidin-2-yl)-ethoxycarbonyl)-L-Phe-L-Nva-(1-S-cyclohexylmethyl-2-S-hydroxy-5-(2-pyridyl))-n-pentylamide Melting point: 115°–125° C.
MS (FAB): 678 (M+ +1)
$R_f$ 0,52 ($CH_2Cl_2/CH_3OH/H_2O/CH_3COOH$ 100/50/10/5)

EXAMPLE 33

N-(2-(4-tert.-Butoxycarbonylpiperazin-1-yl)-ethoxycarbonyl)-L-Phe-L-Nva-(1-S-cyclohexylmethyl-2-S-hydroxy-5-(2-pyridyl))-n-pentylamide

MS (FAB): 779 (M+ +1)

EXAMPLE 34

N-(2-(2-Pyridyl)-ethoxycarbonyl)-L-methionin sulfone L-norvaline-(1-S-cyclohexylmethyl)-2-S-hydroxy-5-(2-pyridyl))-n-pentylamide
Melting point: 79°-81° C.
MS (FAB): 689 (M++1)

EXAMPLE 35

N-(2-(N-tert.-Butoxycarbonyl-2-piperidyl)-ethoxycarbonyl)-L-Phe-L-Nva-(1-S-cyclohexylmethyl-2-S-hydroxy-5-(2-pyridyl)-pentylamide
The title compound was prepared from the compounds of Examples 5 and 24 by the process described in Example 2.
MS (FAB): 778 (M++1)
Melting point: 59°-61° C.

EXAMPLE 36

N-(2-(2-Piperidyl)-ethoxycarbonyl)-L-Phe-L-Nva-(1-S-cyclohexylmethyl-2-S-hydroxy-5-(2-pyridyl)-pentylamide
The title compound was prepared from the compound described in Example 34 by the process described in Example 5 with subsequent purification by chromatography on silica gel.
MS (FAB): 678 (M++1)
$R_f$ 0,30 ($CH_2Cl_2$/MeOH 9:1)

EXAMPLE 37

N-(2-(N-tert.-Butoxycarbonyl-4-piperidyl)-ethoxycarbonyl)-L-Phe-L-Nva-(1-S-cyclohexylmethyl-2-S-hydroxy-5-(2-pyridyl)-pentylamide
The title compound was prepared from the compounds of Examples 23 and 5 by the process described in Example 2.
MS (FAB): 778 (M++1)
Melting point: 65°-72° C.

EXAMPLE 38

N-(2-(4-Piperidyl)-ethoxycarbonyl)-L-Phe-L-Nva-(1-S-cyclohexylmethyl-2-S-hydroxy-5-(2-pyridyl)-pentylamide
The title compound was prepared from the compound described in Example 36 by the process described in Example 5 with subsequent purification by chromatography on silica gel.
MS (FAB): 678 (M++1)
$R_f$ 0,22 ($CH_2CH_2$/methanol 9:1)

EXAMPLE 39

N-(2-(N-tert.-Butoxycarbonyl-2-piperidyl)-ethoxycarbonyl)-L-Phe-L-His-(1-S-cyclohexylmethyl-2-S-hydroxy-5-(2-pyridyl))-pentylamide
Melting point: 98° C. (decomposition)
MS (FAB): 817 (M++1)
$R_f$ 0,33 ($CH_2Cl_2$/MeOH 9:1)

EXAMPLE 40

N-(2-(2-Piperidyl)-ethoxycarbonyl)-L-Phe-L-His-(1-S-cyclohexylmethyl-2-S-hydroxy-5-(2-pyridyl))-pentylamide
MS (FAB): 717 (M++1)

EXAMPLE 41

N-(2-Morpholin-4-yl)-ethoxycarbonyl-L-Phe-L-His-(1-S-cyclohexylmethyl-2-S-hydroxy-5-(2-pyridyl))-pentylamide
Melting point: 70°-81° C.
$R_f$ 0,72 ($CH_2Cl_2$/MeOH 9:1)

EXAMPLE 42

N-(2,2,5,5-Tetramethyl-1,3-thiazolidine-4-yl-carbonyl)-L-phenylalanyl-L-norvalyl-(1-S-cyclohexylmethyl-2-S-hydroxy-5-(2-pyridyl))-pentylamid
The title compound was prepared from the compound described in example 5 and N-(2,2,5,5-Tetramethyl-1,3-thiazolidine-4-yl-carbonyl)-L-phenylalanin by the process described in example 2.
MS (FAB) 695 (M+1)
$R_f$ 0,51 ($CH_2Cl_2$/MeOH)

EXAMPLE 43

N-(2-(4-Tert.-butoxycarbonylpiperazin-1-yl)-ethoxycarbonyl)-L-Phe-L-His-(1-S-cyclohexylmethyl-2-S-hydroxy-5-(2-pyridyl))-n-pentylamide
The title compound was prepared from the compounds of Examples 13 and 28 by the process described in Example 2
MS (FAB) 817 (M+1)
Melting point: 82°-89° C.

EXAMPLE 44

N-(2-Piperazin-1-yl)-ethoxycarbonyl-L-Phe-L-His-(1-S-cyclohexylmethyl-2-S-hydroxy-5-(2-pyridyl))-n-pentylamide
The title compound was prepared from the compound of Example 43 by the process described in Example 5 MS (FAB) 717 (M+1)

EXAMPLE 45

N-Nicotinoyl-L-Phe-L-His-(1-S-cyclohexylmethyl-2-S-hydroxy-5-(2-pyridyl))-pentylamide
The title compound was prepared from the compound of Example 5 and N-Nicotinoyl-L-Phe by the process described in Example 14 and subsequent treated with $CF_3COOH$ as described in Example 15. The yield after chromatography was 412 mg.
MS (FAB) 666 (M+1)
Melting point: 103°-110° C.
$R_f$ 0,18 ($CH_2Cl_2$/MeOH 9:1)

We claim:
1. A compound of the formula (I)

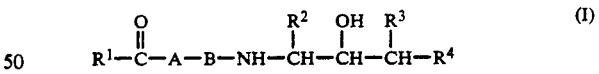

wherein
R$^1$ is selected from the group consisting of Het-($C_1$–$C_6$)-alkyl, Het-($C_1$–$C_6$)-alkoxy, and Het-mercapto-($C_1$–$C_6$)-alkyl, wherein Het is a 5- to 7-membered heteromonocyclic ring, which comprises one or two members from the group consisting of N, O, and S as hetero elements and no other hetero elements;
R$^2$ is ($C_4$–$C_7$)-cycloalkyl-($C_1$–$C_4$)-alkyl;
R$^3$ is selected from the group consisting of hydrogen and hydroxyl;
R$^4$ is a radical of the formula (II)

wherein
R$^5$ is hydrogen;

D is selected from the group consisting of a 2-pyridine radical, a 3-pyridine radical, and a 4-pyridine radical;

m is 1; and

A and B independently denote a divalent radical selected from the group consisting of phenylalanine, histidine, methionine, leucine, isoleucine, valine, methionine sulfone, methionine sulfoxide, norvaline, and norleucine, or a physiologically tolerated salt thereof.

2. A compound according to claim 1, wherein said Het is benzo-fused, aromatic, partly hydrogenated, or completely hydrogenated.

3. A compound according to claim 1, wherein said Het ring is substituted by 1 or 2 identical or different radicals from the group consisting of $(C_1-C_6)$-alkyl, $(C_1-C_6)$-alkoxycarbonyl, amino, and oxido.

4. A method for the treatment of hypertension comprising administering to a subject an effective amount of a compound of formula (I) as claimed in claim 1, or a physiologically tolerated salt thereof.

5. A pharmaceutical composition for the treatment of hypertension comprising an effective amount of a compound of formula (I) as claimed in claim 1, or a physiologically tolerated salt thereof, and a pharmaceutically acceptable vehicle.

* * * * *